(12) United States Patent
Marchi et al.

(10) Patent No.: US 9,433,462 B2
(45) Date of Patent: Sep. 6, 2016

(54) TISSUE FUSION SYSTEM, APPARATUS AND METHOD

(71) Applicant: Cook Medical Technologies LLC, Bloomington, IN (US)

(72) Inventors: Benjamin Marchi, Lafayette, IN (US); Jarin Kratzberg, Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 164 days.

(21) Appl. No.: 13/794,965

(22) Filed: Mar. 12, 2013

(65) Prior Publication Data

US 2014/0180287 A1     Jun. 26, 2014

Related U.S. Application Data

(60) Provisional application No. 61/740,988, filed on Dec. 21, 2012.

(51) Int. Cl.
*A61B 18/14* (2006.01)
*A61B 18/00* (2006.01)

(52) U.S. Cl.
CPC ....... *A61B 18/1447* (2013.01); *A61B 18/1445* (2013.01); *A61B 2018/00595* (2013.01)

(58) Field of Classification Search
CPC ................. A61B 18/1447; A61B 2018/00595
See application file for complete search history.

(56) References Cited

U.S. PATENT DOCUMENTS

| 5,330,471 A | 7/1994 | Eggers |
| 5,415,657 A | 5/1995 | Taymor-Luria |
| 5,569,243 A | 10/1996 | Kortenbach et al. |
| 6,010,523 A | 1/2000 | Sabin et al. |
| 6,139,563 A | 10/2000 | Cosgrove, III et al. |
| 6,394,964 B1 | 5/2002 | Sievert, Jr. et al. |
| 6,964,662 B2 | 11/2005 | Kidooka |
| 7,182,763 B2 | 2/2007 | Nardella |
| 7,462,175 B2 | 12/2008 | Chang et al. |
| 7,621,910 B2 | 11/2009 | Sugi |
| 7,972,333 B2 | 7/2011 | Nishimura |
| 8,114,017 B2 | 2/2012 | Bacher |
| 8,221,418 B2 | 7/2012 | Prakash et al. |
| 2009/0062795 A1 | 3/2009 | Vakharia et al. |
| 2011/0251612 A1* | 10/2011 | Faller et al. ............. 606/52 |
| 2011/0251613 A1 | 10/2011 | Guerra et al. |
| 2012/0303025 A1* | 11/2012 | Garrison ............... 606/51 |

FOREIGN PATENT DOCUMENTS

JP     2012/042920     5/2012

* cited by examiner

*Primary Examiner* — Michael Kahelin
(74) *Attorney, Agent, or Firm* — Brinks Gilson & Lione

(57) ABSTRACT

A system for closing a wound tract after performing a percutaneous procedure is provided. The system includes a closure mechanism having a pair of arm portions that are arranged to adjust between an open and closed position. The closure mechanism includes an electrode that is electrically connected to a power source configured to provide an electrical current or waveform to the electrode. The closure mechanism can be delivered to the wound tract, where the arm portions are adjusted to their open configuration. The arm portions can be moved into engagement with the tissue surrounding the wound tract, where the arm portions can be opened further or closed to reduce the size of the wound tract. The waveform can be applied to the electrode to cauterize the wound, and the closure mechanism can be retracted.

10 Claims, 8 Drawing Sheets

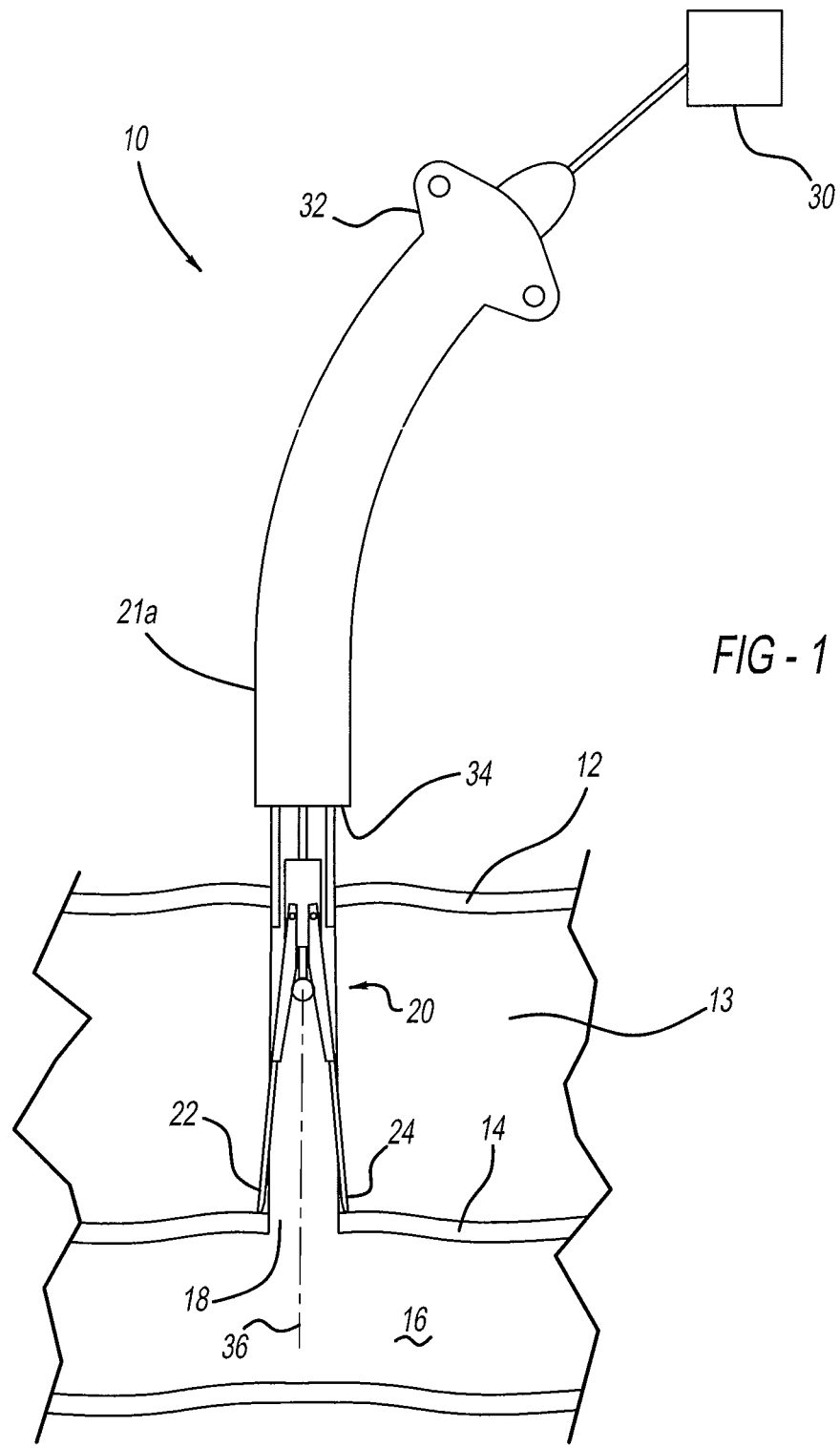

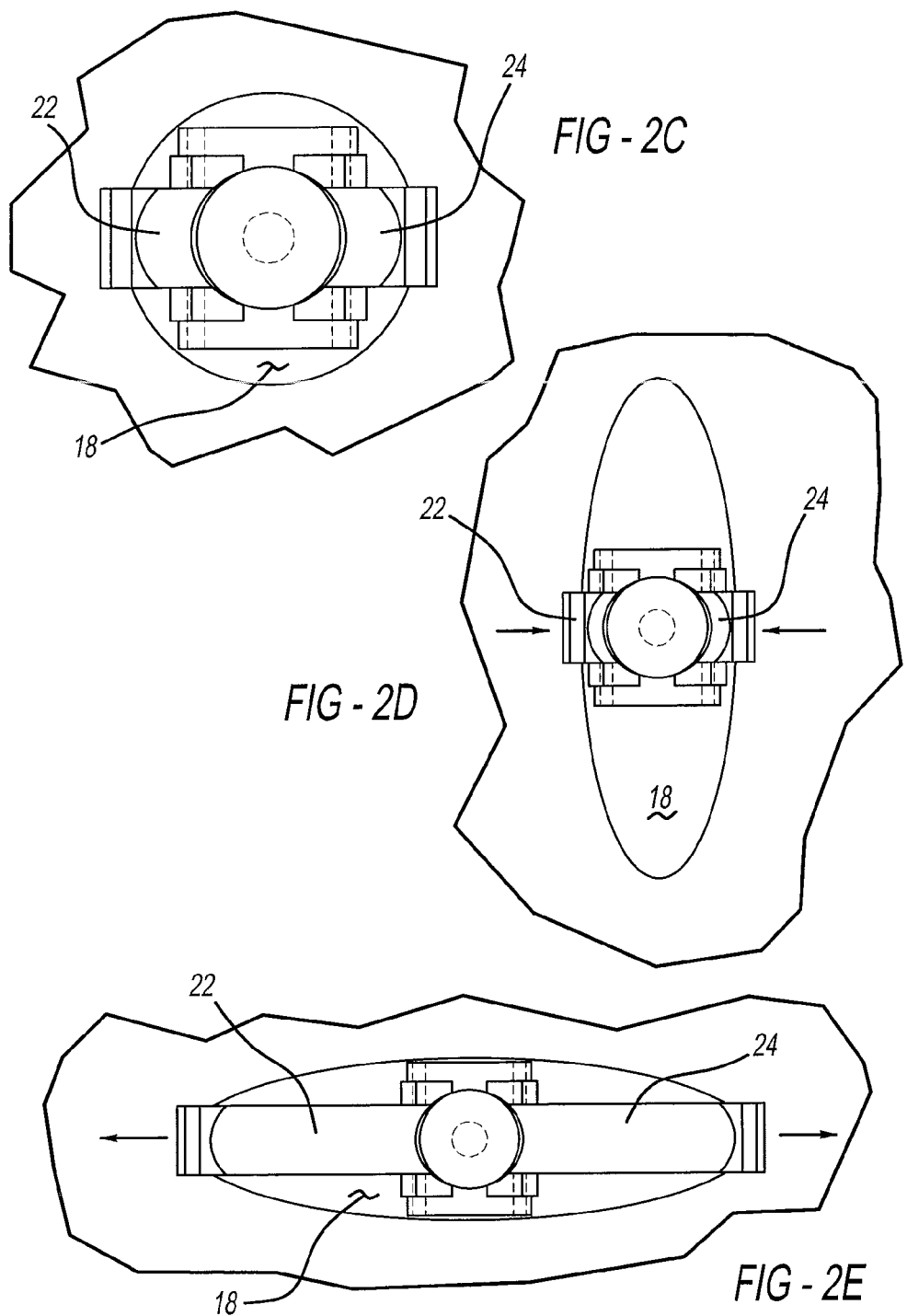

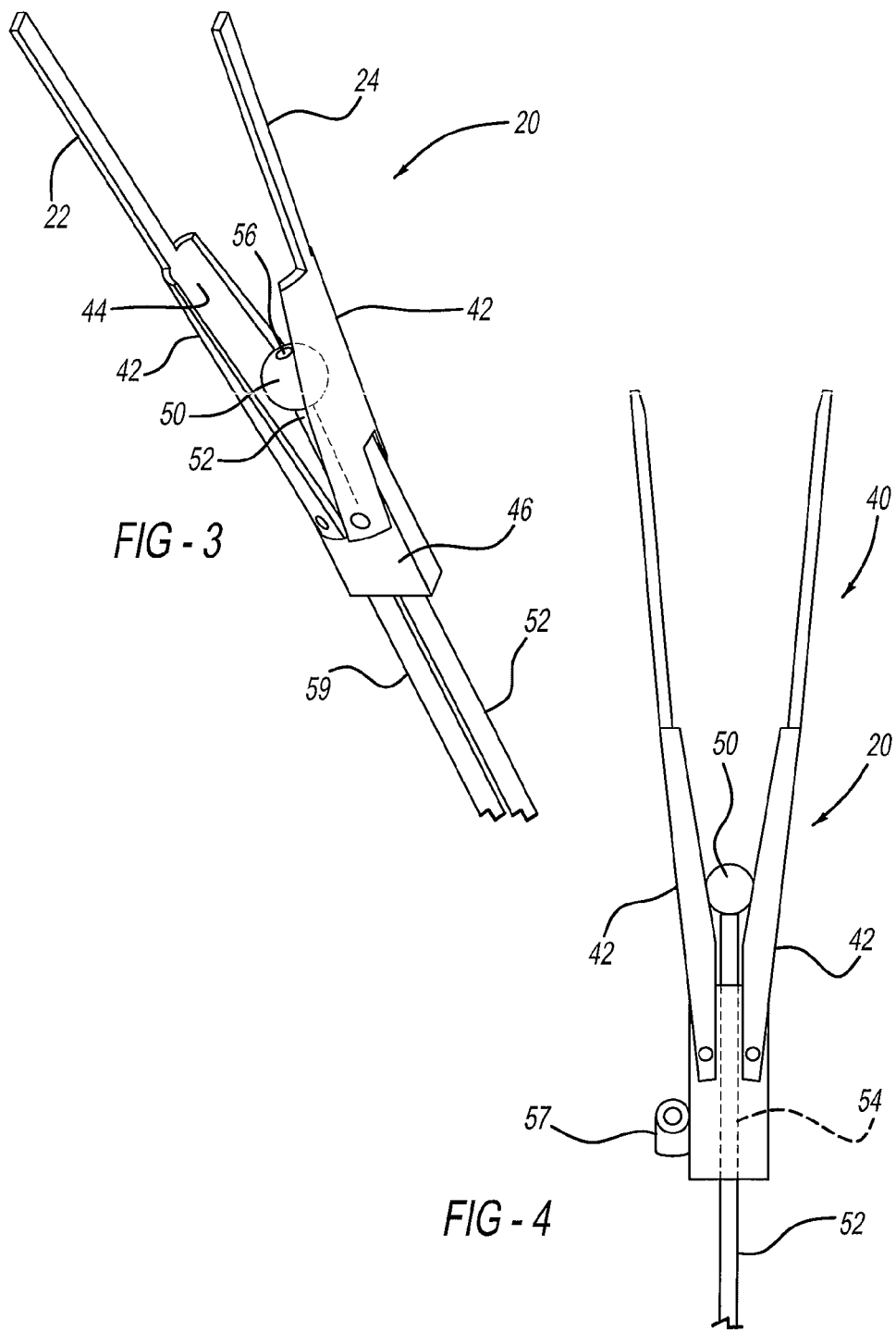

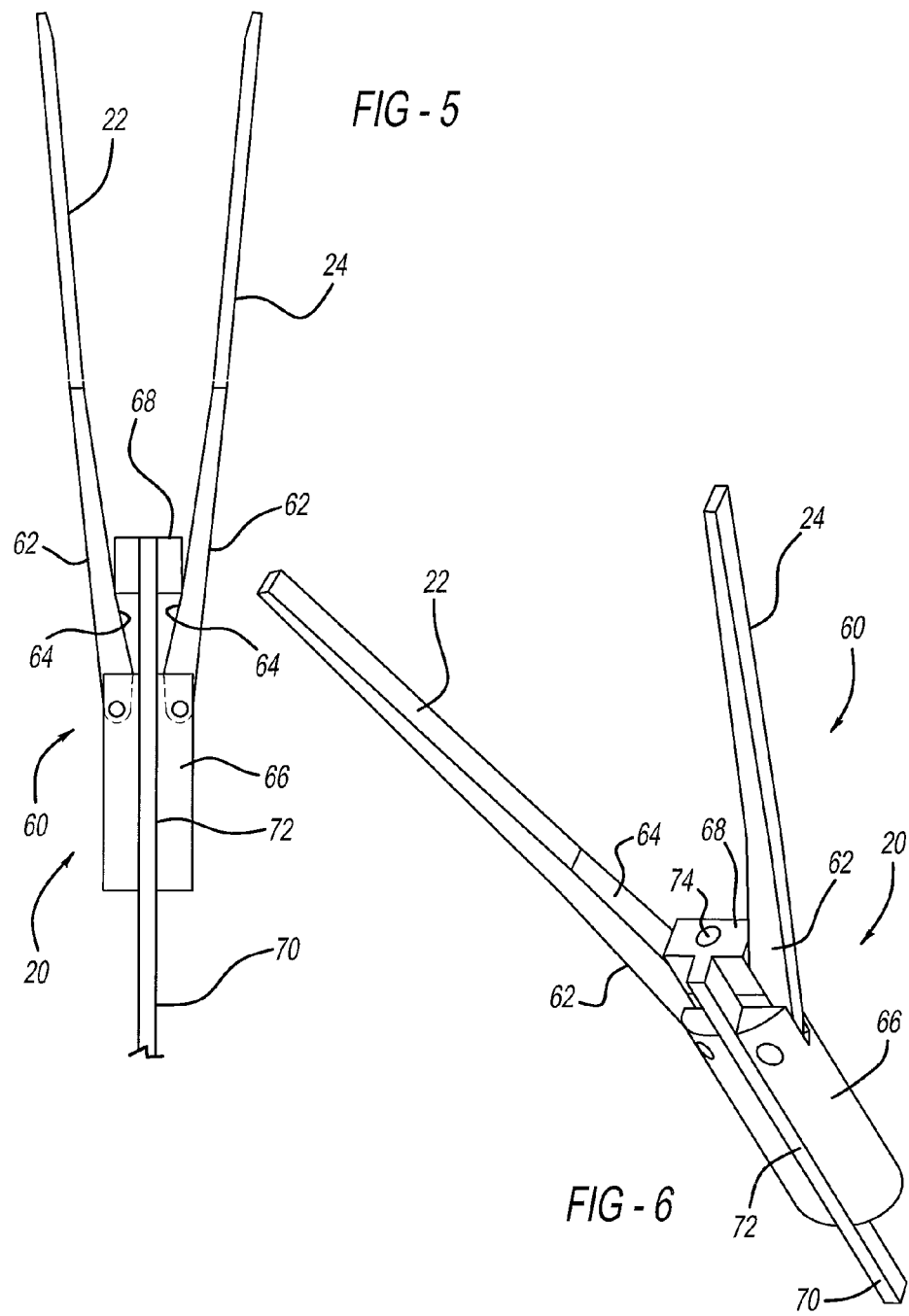

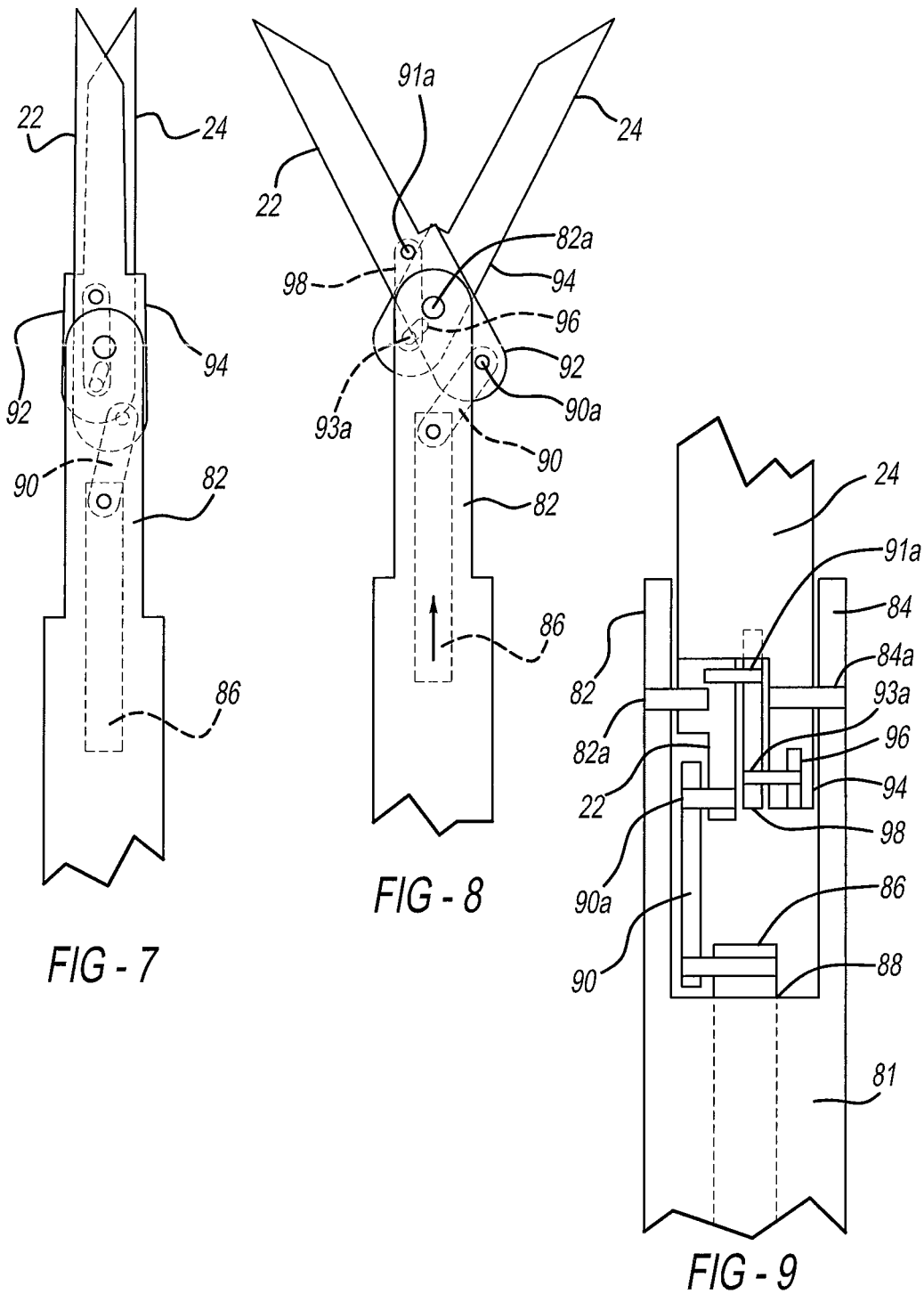

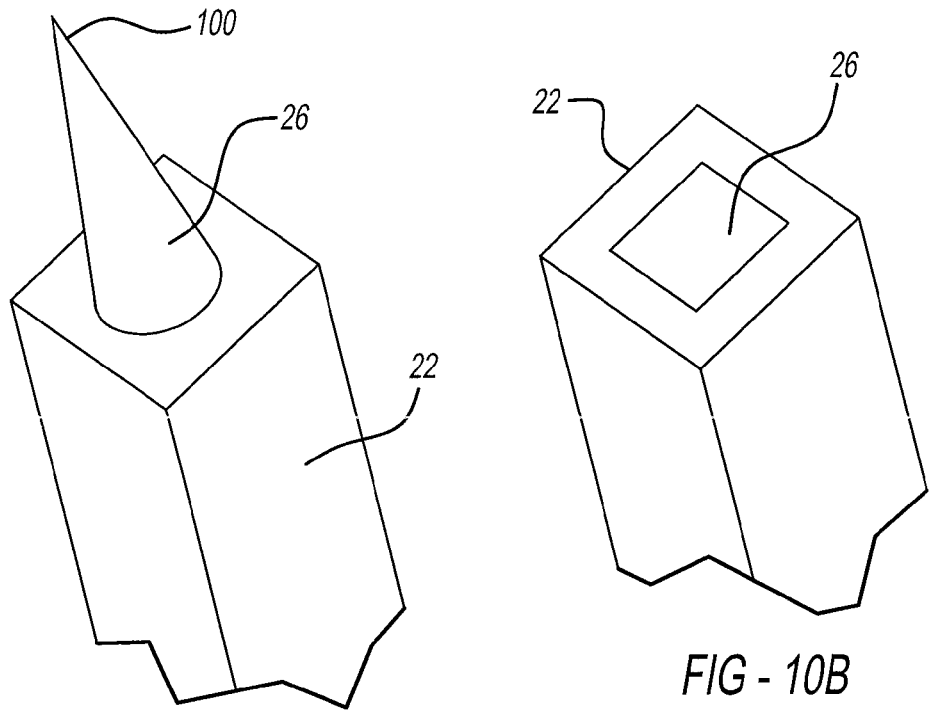
FIG - 10A
FIG - 10B
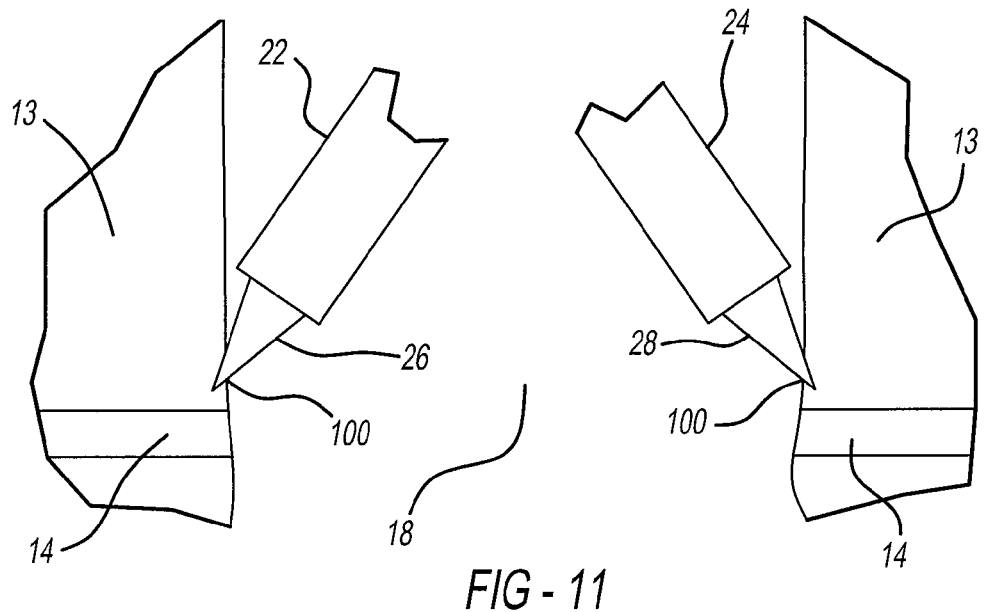
FIG - 11

TISSUE FUSION SYSTEM, APPARATUS AND METHOD

CROSS-REFERENCE TO RELATED APPLICATIONS

This application claims the benefit of U.S. Provisional Application No. 61/740,988, filed on Dec. 21, 2012, entitled "TISSUE FUSION SYSTEM, APPARATUS AND METHOD," the entire contents of which are incorporated herein by reference.

BACKGROUND

The present embodiments relate generally to a system, apparatus, and method for closing a wound site and, more particularly, for closing a percutaneous wound using electrosurgical techniques.

Minimally invasive surgery is commonly used for reducing the level of trauma a patient undergoes during a surgical procedure. Generally, minimally invasive surgical techniques involve creating one or more incisions in a patient's skin, where a surgical instrument can then be inserted through the incisions for delivery toward a target site within the body.

Minimally invasive surgery can be used to perform various procedures. One type of procedure is known as peripheral intervention, which generally involves puncturing the patient's skin near a peripheral blood vessel such as, for example, the femoral artery, where a catheter or other elongate medical device can be introduced into the blood vessel and delivered to the target site. At the conclusion of the procedure, the elongate medical device and other instruments can be removed, leaving behind an open percutaneous wound at the surface of the blood vessel. The percutaneous wound size for peripheral access is generally 10 French or lower. Wounds of this size are commonly closed using a staple or suture or other permanent implantation, or by using direct pressure to provide hemostasis. However, these methods leave behind medical structure to keep the wound closed or, in the case of direct pressure, require sustained pressure on the wound. The direct pressure process can also be ineffective for larger sized wound openings.

Another type of wound closure method involves the use of electrocautery. Electrocautery procedures include passing an electric current through the patient's tissue at the location of the wound, resulting in a cauterization and hemostasis. These electrocautery procedures are generally ineffective on larger wound openings.

Minimally invasive procedures can also be used for endovascular aneurysmal and abdominal arterial repairs. These procedures also result in a wound opening after the procedure is concluded. However, the wound size is substantially larger, such as between 12-20 French. The direct pressure method is generally ineffective for wounds of this size, as is electrocautery. One solution is the use of staples, sutures, or other implantation, but this method results in the implantation being left behind, which is undesirable.

Thus, there is a need for a device and method that can cauterize a relatively large wound opening without requiring an implantation to be left behind at the wound site.

SUMMARY

A system for providing hemostasis to a wound tract following a percutaneous medical procedure is provided, the system comprising; a closure mechanism comprising a pair of generally rigid arms arranged for opening and closing, the arms being moveable between an open configuration and a closed configuration for reducing the width of a wound tract; a first electrode disposed on the closure device and moveable into engagement with a the wound tract; a power source electrically connected to the first electrode for providing a current or waveform to the wound tract.

In another form, the system further comprises a means for opening and closing the arms of the closure mechanism.

In another form, the system further comprises a linearly actuated ball mechanism, the arms thereby being moveable between the open configuration and the closed configuration by actuating the ball mechanism.

In another form, the arms each include a tapered flute portion having a concave channel, the ball mechanism includes a ball member disposed between the arm portions, and the arms are opened by translating the ball member proximally along the concave channels to force the arm portions open.

In another form, the system further comprises a tubular sheath and wherein the arms are closed by translating the ball member distally and translating the sheath over the arms to receive the closure mechanism within the lumen to force the arms closed.

In another form, the system further comprises a linear actuated block mechanism, the arms thereby being moveable between the open configuration and the closed configuration by actuating the block mechanism.

In another form, the arm members each include surfaces facing inwardly, the block mechanism includes a block member disposed between the surfaces, and the arms are opened by translating the block member proximally to slide along the surfaces to force the arm members open.

In another form, the arms are closed by translating the block member distally and translating a sheath having a lumen therein over the arms to receive the closure mechanism within the lumen to force the arms closed.

In another form, the system further comprises a linkage mechanism, the arms thereby being moveable between the open and closed configuration by actuating the linkage mechanism.

In another form, the linkage mechanism includes an actuation bar pivotally mounted to a linkage bar, wherein the linkage bar is pivotally mounted to a first arm of the pair of arms, and wherein the first arm is coupled to a second arm of the pair of arms via a scissor linkage bar.

In another form, the arms are opened by translating the actuation bar distally, causing the first arm to open via the linkage bar and the second arm to open via the scissor linkage bar, and the arms are closed by translating the actuation bar proximally to cause the opposite reaction in the linkage mechanism.

In another form, a closure mechanism apparatus for closing a wound tract is provided, the apparatus comprising: a closure mechanism having a base member and a pair of rigid arms pivotally mounted to the base member, the arms being configured for pivoting between an open configuration and a closed configuration for reducing the width of a wound tract; and a first electrode disposed on the closure mechanism, the electrode configured for being electrically connected to a power source and energized to cauterize a wound tract when the width of the wound tract has been reduced by opening or closing the arms.

In another form, the apparatus further comprises a linearly actuated mechanism comprising one of a block member or a ball member disposed between the arm members and including an elongate bar member mounted thereto, wherein the arms are moved toward the open configuration by translating the elongate bar proximally to slide the block or ball member along an inner surface of each of the arm member to force the arm members open, and the arms are closed by advancing a tubular body over the arm members with the block member or ball member disengaged from the arm members.

In another form, the electrode is disposed on the ball member or the block member.

In another form, the apparatus further comprises a linkage mechanism, wherein a first arm of the pair of arms is pivotally mounted to a linkage bar that is pivotally mounted to an actuation bar, and a second arm of the pair of arms is coupled to the first arm via a scissor linkage bar, wherein longitudinal movement of the actuation bar moves the arms between the closed and open configurations.

In another form, a method for closing a wound tract following a percutaneous procedure is provided, the method comprising: inserting a closure mechanism having a pair of generally rigid arms into a patient's body along a wound tract and toward a body cavity, the arms configured for moving between a closed configuration and an open configuration; pivoting the pair of arms of the closure mechanism into the open configuration; engaging the arms with the wound tract; in response to engaging the arms with the wound tract, pivoting the arms to reduce the width of the wound tract; engaging an electrode disposed on the closure mechanism with the wound tract; applying an electrical current or waveform to the wound tract via the electrode to encourage hemostasis of the wound tract; and withdrawing and removing the closure mechanism having the pair of arms from the wound tract in a proximal direction so that wound tract is generally free from a medical implantation.

In another form, the method further comprises, in response to engaging the arms with the wound tract, pivoting the pair of arms into the closed position to reduce the width of the wound tract.

In another form, the method further comprises, in response to engaging the arms with the wound tract, pivoting the pair of arms into a further open configuration to reduce the width of the wound tract.

In another form, the step of engaging an electrode with the wound tract comprises advancing an electrode longitudinally into engagement with the wound tract.

In another form, the method further comprises advancing a sheath over the closure mechanism to surround the arms of the closure mechanism to close the arms.

BRIEF DESCRIPTION OF THE DRAWINGS

FIG. 1 is a schematic view of a system for closing a wound tract, the system having a closure mechanism, with the closure mechanism shown in an open configuration;

FIG. 2C is a top view of the wound tract with the closure mechanism in an open configuration;

FIG. 2D is a top view of the wound tract with the closure mechanism in a closed configuration to close the wound tract;

FIG. 2E is a top view of the wound tract with the closure mechanism in a further open configuration to close the wound tract;

FIG. 3 is an isometric view of a first embodiment of the closure mechanism;

FIG. 4 is a front view of the closure mechanism of FIG. 3;

FIG. 5 is a front view of a second embodiment of the closure mechanism;

FIG. 6 is an isometric view of the closure mechanism of FIG. 5;

FIG. 7 is a front view of a third embodiment of the closure mechanism in a closed configuration;

FIG. 8 is a front view of the closure mechanism of FIG. 7 in an open configuration;

FIG. 9 is a side view of the closure mechanism of FIG. 7;

FIG. 10A is an isometric view of a distal end of an arm member of the closure mechanism having an engagement member disposed at the distal end;

FIG. 10B is an isometric view of a distal end of an arm member of the closure mechanism having an electrode disposed at the distal end; and FIG. 11 is a schematic view of the arm member engaging the tissue surrounding the wound tract.

DETAILED DESCRIPTION

Figure 2A:
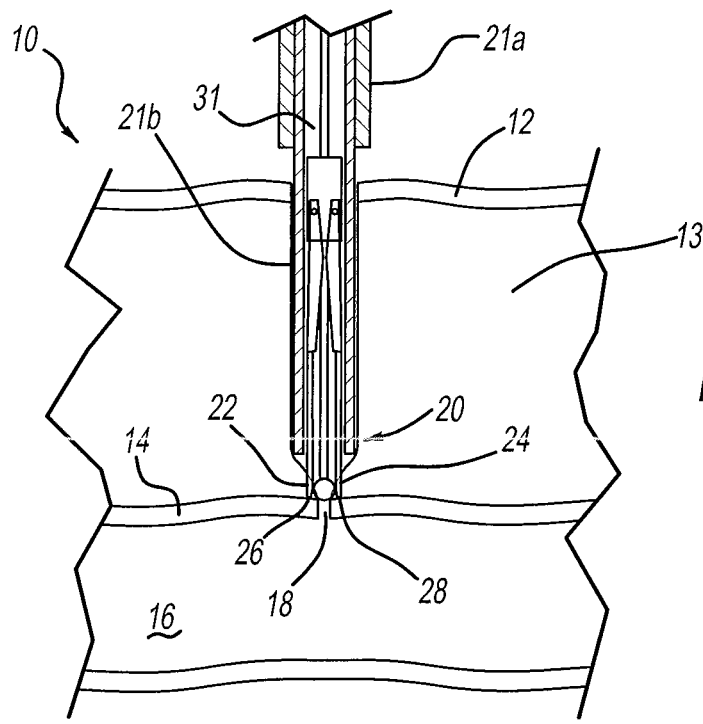
FIG. 2A is a schematic view of the system with the closure mechanism in a closed configuration to close the wound tract.

Referring now to the drawings, FIGS. 1-11 illustrate a system 10 for closing a wound tract following a percutaneous procedure. Percutaneous procedures are known in the art and will not be discussed in detail herein. A minimally invasive percutaneous procedure involves puncturing a patient's skin 12, a muscular fascia or tissue 13, and a wall 14 of a body cavity or blood vessel 16 to obtain percutaneous access to the vessel 16. Upon completion of the procedure, a wound tract 18 results through the skin 12, tissue 13, and wall 14. The wound tract 18 can have a generally elongate and tube like shape as a result of the procedure, as known in the art. Closure of the wound tract 18 is desired and can be completed using the system 10 as described herein. It has been found that providing hemostasis of the tissue 13 adjacent the wall 14 can sufficiently allow the wall 14 and skin 12 to heal.

The system 10 includes a closure mechanism 20 that can be contained within a tubular delivery device 21*aa* having a tubular sheath 21*b*. However, the closure mechanism 20 could also be used without a delivery device 21*aa* or sheath 21*b*, if desired. The delivery device 21*a* or sheath 21*b* can be re-used from the procedure that produced the wound tract 18.

The closure mechanism 20 includes a first arm member 22 and a second arm member 24 that can have both an open configuration (FIG. 1) and a closed configuration (FIG. 2A). The closure mechanism 20 can also include a first electrode 26 attached thereto. In one form, the first arm member 22 has a first electrode 26 at its distal end, and the second arm member 24 has a second electrode 28 at its distal end. However, the electrodes 26 and 28 could be disposed elsewhere on the closure mechanism 20 and second electrode 28 can be optional if a return path is otherwise provided. The closure mechanism 20 is electrically connected to a power source 30 configured for providing an electric current or waveform to the first electrode 26 and for receiving the completed electric circuit through the second electrode 28 or other return path in a manner known in the art. Of course, the circuit could also be completed by running the circuit to a ground rather than back to the power source 30. The system 10 can be either monopolar or bipolar for providing the electric current to the patient's tissue for performing electrocautery.

The arms 22 and 24 can have a generally rigid construction so that they are generally resistant to deformation so that they can cause adjacent tissue to deform upon an application of force by the arms 22 and 24, and can be made from any material known in the art that can provide this generally rigid construction and is suitable for insertion into a patient's body. This rigid construction can aid in the closure of the wound tract 18, because the closing of the arms 22 and 24 will cause the wall 14 to be moved along with the movement of the arms 22 and 24 as they close without deforming the arms 22 and 24 and hindering the closure of the wound tract 18.

In another form, the arms 22 and 24 can be made to open an amount greater than the nominal width of the wound tract 18. In this approach, the arms 22 and 24 will cause the wound tract 18 to become wider in the direction that the arms 22 and 24 are opening, but become narrower in the perpendicular direction. This is due to the resiliency of the muscle or tissue 13 in the wound tract 18, which will tend to maintain a consistent perimeter length, such that expanding the arms will generally convert a generally circular cross-section to a more elongate or ovular cross-section, such that the inner surface of the wound tract 18 will come together.

Figure 2B:
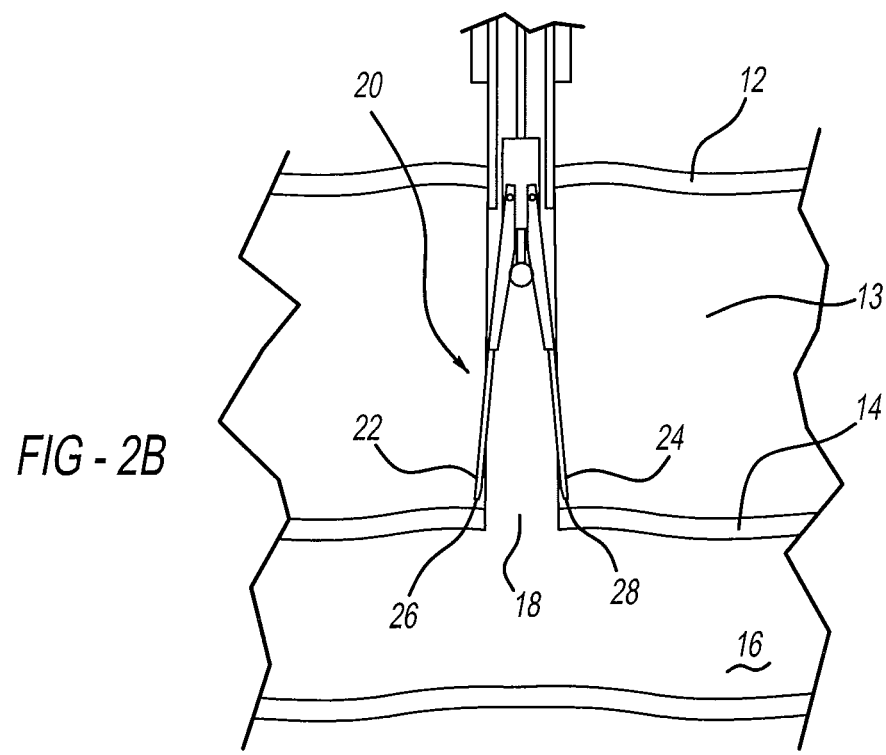
FIG. 2B is a schematic view of the system with the closure mechanism in a further open configuration to close the wound tract.
Figure 2F:
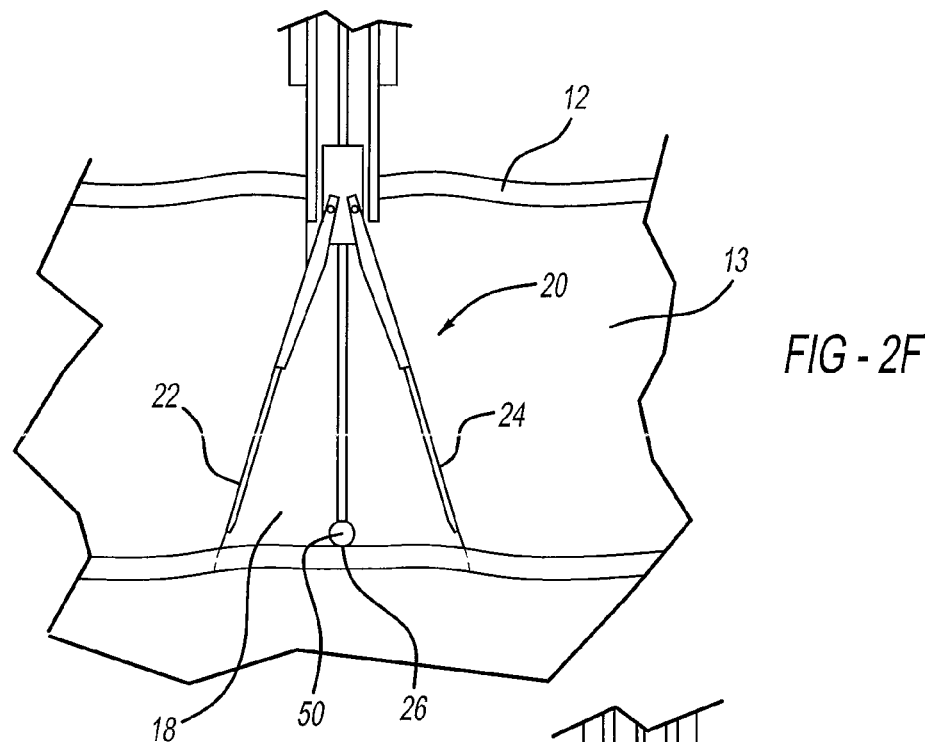
FIG. 2F is a schematic view of the closure mechanism in an open configuration to close the wound tract with a ball mechanism having an electrode advanced toward the wound tract to apply an electric current to the wound tract.
Figure 2G:
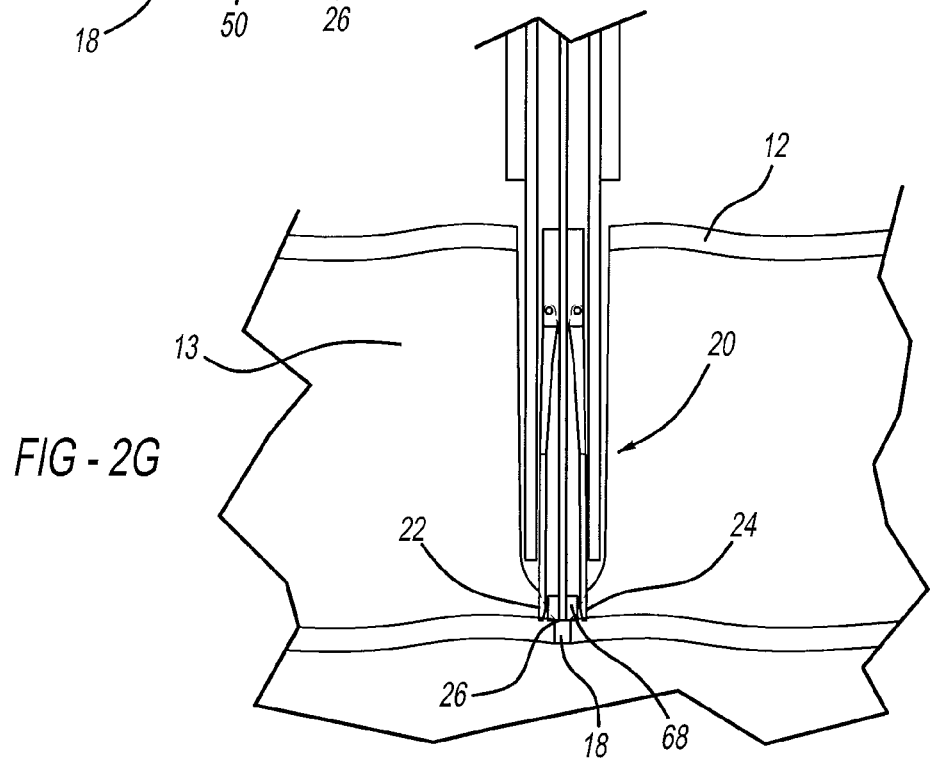
FIG. 2G is a schematic view of the closure mechanism in a closed configuration to close the wound tract with a block mechanism having an electrode advanced toward the wound tract to apply an electric current to the wound tract.

The various open and closed configurations can be seen in FIG. 1 and FIGS. 2A-2G. FIG. 1 illustrates the closure mechanism 20 in an open configuration. FIG. 2A illustrates the closure mechanism 20 in a closed configuration, where the arms 22 and 24 have been closed, having engaged the tissue 13 near the blood vessel wall 14 and reduced the width of the wound tract 18. FIG. 2B illustrates the closure mechanism 20 in a further open configuration, where the arms 22 and 24 have been spread further apart to close the width of the wound tract 18. FIG. 2C illustrates a view looking down on the wound tract 18 with the arms 22 and 24 in an open configuration similar to that shown in FIG. 1. FIG. 2D illustrates a view looking down on the wound tract 18, with arms 22 and 24 in a closed configuration, similar to that shown in FIG. 2A. FIG. 2E illustrates a view looking down on the wound tract 18 with the arms 22 and 24 in a further open configuration similar to that shown in FIG. 2B. As illustrated in the views mentioned above, the arms 22 and 24 can both open and close to close the wound tract 18. FIGS. 2F and 2G illustrates the closure mechanism 20 in an open configuration and closed configuration, respectively, to close the wound tract 18, with the electrode 26 being advanced toward the wound tract to cauterize the wound tract 18.

The delivery device 21a can have a generally tubular shape with a lumen 31 extending therethrough as is common in the art. The delivery device 21a can also include a handle portion 32 at its proximal end and an opening 34 at its distal end. The closure mechanism 20 can be housed within the delivery device 21a for deployment therefrom. Alternatively, the sheath 21b can be disposed within the delivery device 21a for deploying the closure mechanism 20 in a similar manner.

The system 10 can further include a guidewire 36 that is inserted through the wound tract 18 into the blood vessel 16. The guidewire 36 can be the same as the guidewire used in the previously completed percutaneous procedure, or it can be a new guidewire for use with the system 10. The delivery device 21a can be guided along the guidewire 36 in a manner known in the art, or the guidewire 36 can extend entirely through the lumen 31, depending on the type of closure mechanism 20 employed. The guidewire 36 can, alternatively or in addition to be guided along the delivery device 21a, engage a portion of the closure mechanism 20 for guiding the closure mechanism 20 to the target location within the wound tract 18.

In cases where the closure mechanism 20 is inserted without the use of a delivery device, the closure mechanism 20 can be guided along the guidewire 36. However, in one approach, the closure mechanism 20 could be inserted without the use of a guidewire. For example, the target location could be close enough to the patient's skin 14 that a guidewire is not necessary, or an existing sheath or other tube could already be inserted into the wound tract 18, and the closure mechanism 20 could be guided along this sheath.

The closure mechanism 20 can include various types of means or structure for opening the arms 22 and 24 according to various embodiments described herein. With reference to FIGS. 3 and 4, in a first embodiment, the closure mechanism 20 can include a linearly actuated ball mechanism 40. The ball mechanism 40 includes a pair of flute portions 42 disposed along the arms 22 and 24. Each flute portion 42 includes a concave channel 44 extending along the inner surface thereof so that the concave channels 44 of the arms 22 and 24 face each other. The closure mechanism 20 includes a base portion 46 to which the arm portions 22 and 24 are pivotally mounted via a pin, screw, bolt, or other fastener configured for allowing pivotable rotation. The flute portions 42 are arranged to taper toward the base portion 46, such that the distance between the channels 44 is smaller at locations near the base 46 and larger at locations away from the base 46, when the closure mechanism 20 is in both the open and closed configurations.

With reference to FIGS. 3 and 4, the closure mechanism 20 can further include a ball member 50 having a shaft 52 mounted thereto and extending proximally therefrom. The shaft 52 extends through an opening 54 in the base 46 for allowing the shaft 52 to slide therealong. When the arms 22 and 24 of the closure mechanism 20 is in the closed position, the ball member 50 is disposed distally from the base 46 and between the distal ends of the arms 22 and 24, with the arm members 22 and 24 being pivoted closed. The closure mechanism 20 is generally in the closed position when it is housed in the delivery device 21a to reduce the profile of the system 10 for insertion toward the wound tract 18.

To adjust the closure mechanism 20 into the open position, the ball member 50 can be pulled proximally toward the base portion 46, where the ball member 50 will slide across the channels 44 of the flute portions 42. The tapered shape of the flute portions 42 will cause the arm members 22 and 24 to open outwardly as the ball 50 is pulled proximally. The closure mechanism 20 can be adjusted back to the closed position by pushing the ball member 50 distally so that the ball member 50 is no longer forcing the arms 22 and 24 open. The delivery device 21a or sheath 21b can be translated distally to slide over the arms 22 and 24, pivoting them closed, as shown in FIG. 2A.

To open the ball mechanism 40 embodiment of the closure mechanism 20 again, the delivery device 21a can be retracted again, and the ball member 50 can be pulled proximally to open the arms 22 and 24, because the arms 22 and 24 are no longer restricted from opening by the delivery device 21*a*. The above description of the delivery device 21*a* also applies to the sheath 21*b*.

As described above, the closure mechanism 20 includes a first electrode 26 for transmitting an electric current or waveform to adjacent tissue to perform electrocautery. The first electrode 26, as well as the second electrode 28 (if used), can be disposed on the arms 22 and 24, as previously described. However, in another form, the electrode can be disposed on the ball member 50, as shown in FIG. 2F. In this form, the arms 22 and 24 can include a locking mechanism (not shown) for holding the arms 22 and 24 in the open position after the ball member 50 has translated to open them. The ball member 50 can then be advanced distally and into contact with the wound tract 18 that has been closed to apply the electric current or waveform to the wound tract 18. Alternatively, the ball member 50 can be advanced into contact with the wound tract 18 after the arms 22 and 24 have been closed to close the wound tract 18. FIG. 2F shows the arms 22 and 24 in the open position, but it will be appreciated that the arms 22 and 24 could be in the closed position as well with the ball member 50 translated to engage the electrode 26 with the wound tract 18.

The closure mechanism 20 having the ball mechanism 40 can also include structure for allowing the closure mechanism 20 be inserted along the guidewire 36. In one form, the ball member 50 can include a hole 56 (FIG. 3) extending therethrough for being threaded over the guidewire 36. In another form, the base 46 can include a channel portion 57 (FIG. 4) extending therealong through which the guidewire 36 can extend. It will be appreciated that other structure known in the art could be added to the closure mechanism 20 for assisting in delivering it along a guidewire. The particular structures for accepting a guidewire can be applied to other embodiments described herein, if desired.

The closure mechanism 20, in addition to the structure described above, can include a holding member 59 (FIG. 3) having a generally rigid and elongate form and extending proximally therefrom. The holding member 59 can be used to maintain the depth, or adjust the depth if necessary, of the closure mechanism 20 while the various associated structure is pulled or pushed relative to the closure mechanism. For example, the holding member 59 can be held in a fixed position while the ball member 50 is pulled proximally to open the arms so that the closure mechanism 20 will not be pulled along with the ball member 50. The holding member 59 can be in the form of a tube, rod, bar, or other structure known in the art for controlling the depth of a medical device. The above discussion of the holding member 59 can apply to each of the embodiments of the closure mechanism 20 described herein.

With reference to FIGS. 5 and 6, in a second embodiment, the closure mechanism 20 can include a linearly actuated block mechanism 60 for opening and closing the closure mechanism 20. The block mechanism 60 includes a pair of tapered portions 62 of the arms 22 and 24 having generally flat surfaces 64 that face each other. The closure mechanism can include a base portion 66 to which the arms 22 and 24 are pivotally mounted via a fastener such as a pin. The block mechanism 60 includes a block member 68 having a generally rectangular or square shape, and a slide bar 70 extending proximally therefrom. The base member 60 can include a slot extending 72 along its length, where the slot 72 is sized to correspond to the shape of the slide bar 70, allowing the slide bar 70 to translate along the slot 72. The surfaces 64 slant toward the base 66 along the tapered portions 62 such that the distance between the surfaces 64 is smaller at locations near the base 66 and larger at locations farther away from the base 66, in both the open and closed positions.

The tapered shape of the tapered portions 62 allows the block member 68 to be disposed between the distal ends of the arms 22 and 24 when they are in the closed position. When the block member 68 translates toward the base portion 66, it will contact the surfaces 64 of the tapered portions 62 to force the arms 22 and 24 to open. However, it will be appreciated that the arms 22 and 24 could be free from a tapered portion while still allowing the block member 68 to be disposed between them. In this form, the arms 22 and 24 would generally remain in a non-parallel configuration when closed, so that the block member 68 can interact with the slope defined by the non-parallel configuration to thereby open the arms 22 and 24.

The block member 68 can include a cylindrical passage 74 therethrough to allow the guidewire 26 to extend through the passage 74 to assist in delivering and locating the closure mechanism 20 at the wound tract 18.

Similar to the ball mechanism 40, the arms 22 and 24 can be opened by pulling the slide bar 70 proximally toward the user, which pulls the block member 68, causing it to slide across the surfaces 64, which forces the arms 22 and 24 to pivot and open. To close the arms 22 and 24, the block member 68 and delivery device 21*a* can be pushed distally, so the block member 68 is no longer forcing the arms 22 and 24 open, and the delivery device 21*a* can slide over the arms 22 and 24 to pivot them into the closed position, as shown generally in FIG. 2A.

Similar to the ball mechanism 40 and ball member 50, the block member 68 can include the first electrode 26, as shown in FIG. 2G, to translate toward the wound tract 18 after it has been closed to perform electrocautery and provide hemostasis at the wound tract 18. Alternatively, the first electrode 26 and, if used, the second electrode 28 can be disposed at the distal ends of the arms 22 and 24. FIG. 2G shows the arms 22 and 24 in the closed configuration, with the block member 68 advanced to engage the first electrode 26 with the wound tract 18, but it will be appreciated that the block member 68 and electrode 26 can be advanced with the arms 22 and 24 in the open condition, as well.

With reference to FIGS. 7-9, in a third embodiment of the closure mechanism 20, the closure mechanism 20 can include a linkage mechanism 80 as a means for opening and closing the arms 22 and 24. The linkage mechanism 80 can include a base 81 having a first finger portion 82 and a second finger portion 84. The first arm portion 22 is pivotally mounted to the first finger portion 82 at a first pivot point 82*a*, and the second arm portion 24 is pivotally mounted to the second finger portion 84 at a second pivot point 84*a*. The first and second pivot points 82*a* and 84*a* can be generally coaxial so that the arms 22 and 24 pivot from the same point along the base 81.

The linkage mechanism 80 further includes a longitudinal actuation member 86 that extends through an opening 88 in the base. The actuation member 86 includes a link member 90 pivotally mounted to its distal end. The link member 90 is also pivotally mounted to the proximal end of the first arm member 22 at a pivot point 90*a*. More specifically, the first arm member 22 includes a scissor extension 92 that extends proximally from the arm member 22, and the linkage bar 90 is pivotally mounted to the scissor extension 92.

The second arm member 24 includes a second scissor extension 94 that extends proximally therefrom. The second scissor extension 94 includes a slot 96 extending therealong. The linkage mechanism 80 includes a scissor linkage 98 that is pivotally mounted to the first arm member 22, and slidably mounted to the slot 96 in the second scissor extension 94. Thus, the first arm member 22 and second arm member 24 are engaged with each other via the scissor linkage 98, so that opening the arm 22 will cause the arm 24 to open, as well.

To adjust the closure mechanism 20 having the linkage mechanism 80 to the open configuration, the actuating bar 86 is pushed distally. This causes the linkage bar 90 to act on the first arm member 22, causing it to open. The opening of the first arm member 22 causes the second arm member 24 to open as well via the various linkages and pivot points described above and illustrated in FIGS. 7-9. To close the closure mechanism 20, the actuating bar 86 is pulled proximally, which pulls on the linkage bar 90 to pivot the first arm 22 closed. Closing the first arm 22 causes the second arm 24 to close.

Having described the various structure and means for opening and closing the arms 22 and 24 above, the arms 22 and 24 will now be described, which can apply to any of the embodiments described above.

With reference to FIGS. 10A and 11, the arm members 22 and 24 can include an engagement portion 100 at the distal end. The engagement portion 100 can be in the form of a sharp point, a barb, or other structure capable of engaging tissue 13 without necessarily requiring a grasping, pinching, or sandwiching of the tissue 13. The engagement portion 100 of each arm 22 and 24 can engage the tissue 13 at a transverse or normal angle to the tissue, independent of the other arm. In this sense, the engagement portion 100 will generally puncture the tissue 13. Of course, the arms 22 and 24 together can cooperate to grasp or sandwich tissue, in addition to the puncturing engagement.

In one form, the engagement portion 100 and electrodes 26 and 28 can be the same component, such that the electrodes 26 and 28 operate to engage the tissue 24. In another form, the engagement portion 100 and electrodes 26 and 28 can be separate, but arranged such that the electrodes 26 and 28 will contact the tissue 14 when the engagement portions 100 have engaged the tissue 14. However, as shown in FIG. 10B, the arm member 22 (and/or 24) can include the electrode 26 (and/or 28) at a distal end thereof without having an engagement portion 100.

Having described the structure of the system 10 above, the function of the system 10 will now be described.

After concluding the percutaneous procedure, the medical devices associated with the procedure can be removed, leaving the wound tract 18 to be closed. Of course, a tubular member, such as a sheath or a catheter, along with a guidewire, could be left in place for use with the closure mechanism 20. The guide wire 26 is inserted through the skin 14 and into the wound tract 18 to be closed. The delivery device 21a having the closure mechanism 20 housed therein is inserted through the skin 12 along the guide wire 26 through the wound tract 18 and toward the area to be cauterized. The depth of the insertion of the delivery device 21a can be monitored using known methods, such as fluoroscopy, or by using tactile feedback or linear monitoring. Of course, the closure mechanism 20 can be inserted without the use of a delivery device 21a or guidewire 26, if desired. Closure mechanisms 20 having the ball mechanism 40 or block mechanism 60 are preferably inserted with a delivery device 21a or other sheath so that the sheath can be inserted over the arms 22 and 24 to close them, as described above.

When the delivery device 21a is delivered to the wound tract 18, the delivery device 21a (or sheath 21b) can be retracted to expose the closure mechanism 20. The closure mechanism 20 can be adjusted into its open configuration so that the arms 22 and 24 are opened, as described above. For example, the ball mechanism 40 or the block mechanism 60 can be pulled to force the arms 22 and 24 open, or the linkage mechanism 80 can be opened by pushing on the actuation member 86.

Once the arms 22 and 24 are in the open configuration, the closure mechanism 20 can be advanced toward the tissue 13 near the wall 14 of the wound tract 18. The engaging portions 100 and electrodes 26 and 28 can be advanced into the tissue 13 surrounding the wound tract 18, thereby engaging the tissue 13, as shown in FIG. 1. The surgeon can generally detect that the arms 22 and 24 have engaged the tissue 13 due to tactile feedback, such that the surgeon will sense resistance while pushing on the closure mechanism 20.

The closure mechanism can then be actuated to close the arms 22 and 24. As described above, closing the arms 22 and 24 depends on the type of closure mechanism 20. For example, for the ball mechanism 40 and block mechanism 60, the ball 50 or block 68, respectively, can be pushed distally so that the ball 50 or block 68 are no longer forcing the arms 22 and 24 open. The delivery device 21a (or sheath thereof) can then be pushed distally so that it will surround the arms 22 and 24 and pivot them into the closed position. In the case of the linkage mechanism 80, the actuation bar 86 can be pulled proximally to close the arms 22 and 24. The engagement portions 100 of the arms 22 and 24 will stay engaged with the tissue 13 while closing, and will move the tissue 13 toward a closed position, substantially reducing the size of the wound tract 18.

Alternatively, the arms 22 and 24 can be made to open an additional amount via additional actuation causing opening of the closure mechanism 20. The additional outward force of the arms 22 and 24 will cause the tissue 13 to spread in the direction of the arms 22 and 24 being opened, thereby causing the wound tract 18 to close in the direction generally perpendicular to the direction of the arms 22 and 24. In this approach, the arms portions 22 and 24 could be free of the engagement portions 100, because pushing on the tissue 13 of the wound tract can occur without the need to pull the tissue 13 along with the movement of the arms 22 and 24.

With the wound tract 18 closed by either opening or closing the arms 22 and 24, an electric current or waveform can be applied through the closure device 20 in a manner known in the art. The current can be supplied from the power source 30 through the first electrode 26. Because the electrodes 26 and 28 (if used) are engaging the patient's tissue 13, the tissue 13 will act as a resistor and become heated. The return path can be provided through the second electrode 28 to return to the power source 30 and complete the circuit. In another form, the return path can be provided by a pad attached to the patient's body and connected to a ground or the power source, as known in the art. The current or waveform applied to the tissue 13 at the wound tract 18 that has been reduced will cause the wound tract 18 to become cauterized, which will thereby provide hemostasis.

In the case where the first electrode 26 is disposed on the ball member 50 or block member 68, the ball member 50 or block member 68 can be advanced toward the tissue 13 of the wound tract 18 that has been closed, either by opening the arms 22 and 24 or closing the arms 22 and 24. In the case where the arms 22 and 24 have been opened to close the wound tract 18, the arms 22 and 24 can be kept open via a locking mechanism so that when the block member 68 or ball member 50 is moved distally toward the closed tissue 13, the arms 22 and 24 will remain open to close the tissue. In the case where the arms 22 and 24 are closed to close the wound tract 18, the ball member 50 or block member 68 is no longer holding the arms 22 and 24 open.

Upon completion of cauterizing the wound tract 18 and providing hemostasis, the delivery device 21a and the closure mechanism 20 can then be withdrawn from the patient's body. Upon withdrawal from the patient's body, the incision in the skin 12 from the minimally invasive procedures can be closed using known methods, such as stitches or sutures at the exterior surface of the patient's body, or through direct pressure, if desired. The use of the system 10 and closure mechanism 20 described above thereby operates to provide hemostasis at the wound tract 18 without necessarily requiring structure left behind at the wound tract 18, such as staples, sutures, or the like, thereby reducing instances of trauma that can be experienced by the patient after having a percutaneous procedure performed. The ability to leave no long term implant behind is highly desirable.

The above described system 10 is highly scalable due to the opening and closing or the arms 22 and 24. The surgeon can determine, based on the size of the wound tract 18, how much to open the arms 22 and 24. For a smaller wound tract 18, the arms 22 and 24 can be opened a small amount by adjusting the degree to which the closure mechanism 20 is adjusted. Similarly, for a larger wound tract 18, the arms 22 and 24 can be opened a larger amount.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A closure mechanism apparatus for closing a wound tract, the apparatus comprising:
    a closure mechanism having a base member and a pair of rigid arms each individual arm of the pair of rigid arms pivotally mounted at a pivot point to the base member and being longitudinally and laterally fixed relative to the base member at the pivot point, the arms being configured for pivoting between an open configuration and a closed configuration for reducing the width of a wound tract, wherein the pivot point comprises a single pivot point shared by the pair of rigid arms or a dedicated pivot point for each individual arm;
    a first electrode disposed on the closure mechanism, the electrode configured for being electrically connected to a power source and energized to cauterize a wound tract when the width of the wound tract has been reduced by opening or closing the arms; and
    a linearly actuated mechanism comprising one of a block member or a ball member disposed between the arm members and including an elongate bar member mounted thereto and being extendable between the arm members, wherein the arms are moved toward the open configuration by retracting the elongate bar proximally to slide the block or ball member along an inner surface of each of the arm members to force the arm members open, and the arms are closed by advancing a tubular body over the arm members with the block member or ball member disengaged from the arm members, wherein the tubular body is moveable relative to the block member or ball member.

2. The apparatus of claim 1 further comprising:
    a power source electrically connected to the first electrode for providing a current or waveform to the wound tract.

3. The apparatus of claim 1 further comprising a means for opening and closing the arms of the closure mechanism.

4. A closure mechanism apparatus for closing a wound tract, the apparatus comprising:
    a closure mechanism having a base member and a pair of rigid arms each individual arm of the pair of rigid arms pivotally mounted at a pivot point to the base member and being longitudinally and laterally fixed relative to the base member at the pivot point, the arms being configured for pivoting between an open configuration and a closed configuration for reducing the width of a wound tract, wherein the pivot point comprises a single pivot point shared by the pair of rigid arms or a dedicated pivot point for each individual arm;
    a first electrode disposed on the closure mechanism, the electrode configured for being electrically connected to a power source and energized to cauterize a wound tract when the width of the wound tract has been reduced by opening or closing the arms;
    a linearly actuated ball mechanism having a ball member coupled to a shaft that is independently moveable in both a proximal and distal direction with the shaft extending between the arms, the arms thereby being moveable from a closed configuration to an open configuration by retracting the ball member.

5. The apparatus of claim 4, wherein the arms each include a tapered flute portion having a concave channel being curved in a plane that is transverse to a direction of linear actuation of the ball mechanism, the ball member is disposed between the arms, and the arms are opened by retracting the ball member proximally along the concave channels to force the arms open, wherein the arms open in response to retraction of the ball member.

6. The apparatus of claim 5 further comprising a tubular sheath and wherein the arms are closed by translating the ball member distally and translating the sheath over the arms to receive the closure mechanism within the lumen to force the arms closed, wherein the sheath is moveable relative to the ball member and shaft.

7. A closure mechanism apparatus for closing a wound tract, the apparatus comprising:
    a closure mechanism having a base member and a pair of rigid arms each individual arm of the pair of rigid arms pivotally mounted at a pivot point to the base member and being longitudinally and laterally fixed relative to the base member at the pivot point, the arms being configured for pivoting between an open configuration and a closed configuration for reducing the width of a wound tract, wherein the pivot point comprises a single pivot point shared by the pair of rigid arms or a dedicated pivot point for each individual arm;
    a first electrode disposed on the closure mechanism, the electrode configured for being electrically connected to a power source and energized to cauterize a wound tract when the width of the wound tract has been reduced by opening or closing the arms; and
    a linear actuated block mechanism having a block member coupled to a longitudinally extending shaft that is independently moveable in both a proximal and distal direction with the shaft extending between the arms, the arms thereby being moveable from a closed configuration to an open configuration by retracting the block member.

8. The apparatus of claim 7, wherein the arms each include surfaces facing inwardly, the block member is disposed between the surfaces, and the arms are opened by retracting the block member proximally to slide along the surfaces to force the arms open, wherein the arms open in response to retraction of the ball member.

9. The apparatus of claim 8, wherein the arms are closed by translating the block member distally and translating a sheath having a lumen therein over the arms to receive the closure mechanism within the lumen to force the arms closed, wherein the sheath is moveable relative to the block member and shaft.

10. A closure mechanism apparatus for closing a wound tract, the apparatus comprising:

a closure mechanism having a base member and a pair of rigid arms pivotally mounted to the base member, the arms being configured for pivoting between an open configuration and a closed configuration for reducing the width of a wound tract; and a first electrode disposed on the closure mechanism, the electrode configured for being electrically connected to a power source and energized to cauterize a wound tract when the width of the wound tract has been reduced by opening or closing the arms;

a linearly actuated mechanism comprising one of a block member or a ball member disposed between the arm members and including an elongate bar member mounted thereto, wherein the arms are moved toward the open configuration by translating the elongate bar proximally to slide the block or ball member along an inner surface of each of the arm members to force the arm members open, and the arms are closed by advancing a tubular body over the arm members with the block member or ball member disengaged from the arm members;

wherein the electrode is disposed on the ball member or the block member.

* * * * *